United States Patent [19]

Schoolman

[11] Patent Number: 4,651,201
[45] Date of Patent: Mar. 17, 1987

[54] STEREOSCOPIC ENDOSCOPE ARRANGEMENT

[76] Inventor: Arnold Schoolman, 6420 Prospect, Kansas City, Mo. 64132

[21] Appl. No.: 671,437

[22] Filed: Nov. 14, 1984

Related U.S. Application Data

[63] Continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.⁴ .............................................. H04N 7/18
[52] U.S. Cl. ......................................... 358/98; 358/88
[58] Field of Search ................... 358/88, 901, 98, 3, 358/181; 128/4–11, 303.15

[56] References Cited

U.S. PATENT DOCUMENTS

| | | | |
|---|---|---|---|
| 2,995,156 | 10/1960 | Heilig | 358/88 |
| 3,520,887 | 7/1970 | Tasaki et al. | 358/901 X |
| 3,655,259 | 4/1972 | Miyauchi et al. | 128/6 X |
| 3,670,097 | 6/1972 | Jones | 358/91 |
| 3,784,738 | 1/1974 | Natter | 358/88 X |
| 3,883,689 | 5/1975 | Mansour et al. | 358/227 |
| 3,919,475 | 11/1975 | Dukich et al. | 358/210 |
| 3,923,370 | 12/1975 | Mostrom | 350/619 |
| 3,940,204 | 2/1976 | Withrington | 350/3.72 |
| 3,976,840 | 8/1976 | Cleveland et al. | 179/2 DP |
| 4,028,725 | 6/1970 | Lewis | 358/103 |
| 4,034,401 | 7/1977 | Mann | 358/93 |
| 4,051,802 | 9/1977 | Dukich et al. | 440/6 |
| 4,061,135 | 12/1977 | Wildran et al. | 128/6 |
| 4,115,802 | 9/1978 | Kramer et al. | 358/93 |
| 4,153,913 | 5/1979 | Swift | 358/93 |
| 4,160,263 | 7/1979 | Christy et al. | 358/1 |
| 4,242,703 | 12/1980 | Tsuboshima et al. | 358/150 |
| 4,246,607 | 1/1981 | Vijverberg | 358/111 |
| 4,247,908 | 1/1981 | Lockhart, Jr. et al. | 364/900 |
| 4,266,271 | 5/1981 | Chamoff et al. | 364/200 |
| 4,277,837 | 7/1981 | Stuckert | 364/900 |
| 4,310,849 | 1/1982 | Glass | 358/88 |
| 4,331,132 | 5/1982 | Mukasa | 358/98 X |
| 4,345,315 | 8/1982 | Cadotte et al. | 364/900 |
| 4,360,875 | 11/1982 | Behnke | 364/436 |
| 4,395,731 | 7/1983 | Schoolman | 358/88 |
| 4,398,799 | 8/1983 | Swift | 350/638 |
| 4,433,675 | 2/1984 | Konoshima | 128/6 |
| 4,436,087 | 3/1984 | Ouchi | 128/6 |
| 4,437,458 | 3/1984 | Upsher | 128/11 |
| 4,440,157 | 4/1984 | Shishido | 128/6 |
| 4,444,462 | 4/1984 | Ono et al. | 350/96.25 |
| 4,452,236 | 6/1984 | Utsugi | 128/4 |
| 4,461,280 | 7/1984 | Baumgartner | 128/1.2 |
| 4,461,281 | 7/1984 | Carson | 128/3 |
| 4,461,282 | 7/1984 | Ouchi et al. | 128/4 |

OTHER PUBLICATIONS

3D Survey System, Underground Surveys Corp. Feb.'74.
Aviation Week & Space Technology, Oct. 11, 1983, p. 133, (Vimad Device).

Primary Examiner—Howard W. Britton
Assistant Examiner—Victor R. Kostak
Attorney, Agent, or Firm—Litman, Day & McMahon

[57] ABSTRACT

A stereoscopic endoscope includes a sheath for insertion into the body of a patient and a pair of image guides and an illumination or light guide extending through the sheath. The image guides and light guide are preferably formed of optical fibers to facilitate flexibility of the endoscope. The image guides optically connect with a stereoscopc viewer for three dimensional viewing of a site within the body. The viewer includes couplings for attaching miniaturized video cameras, the cameras in turn being connected to a head worn stereoscopic video display. In addition, the video signals representing the images gathered by the endoscope may be displayed on remote monitors or recorded by a video recorder. The endoscope may include other channels extending through the sheath such as water, air, gas, other fluid channels with associated valves and/or a channel for receiving an endoscopic surgical tool.

24 Claims, 10 Drawing Figures

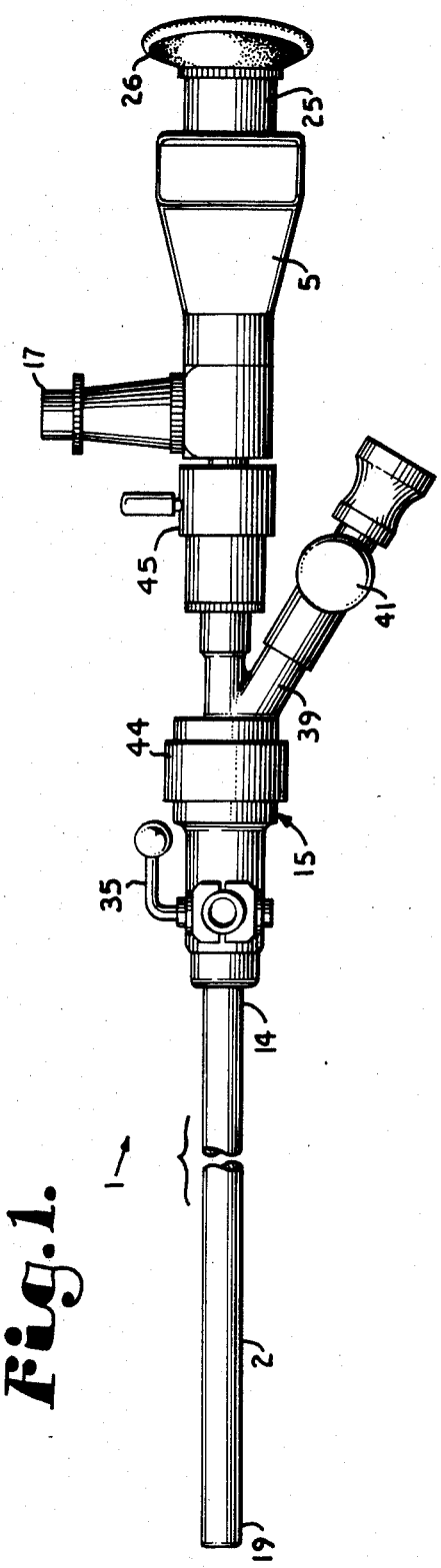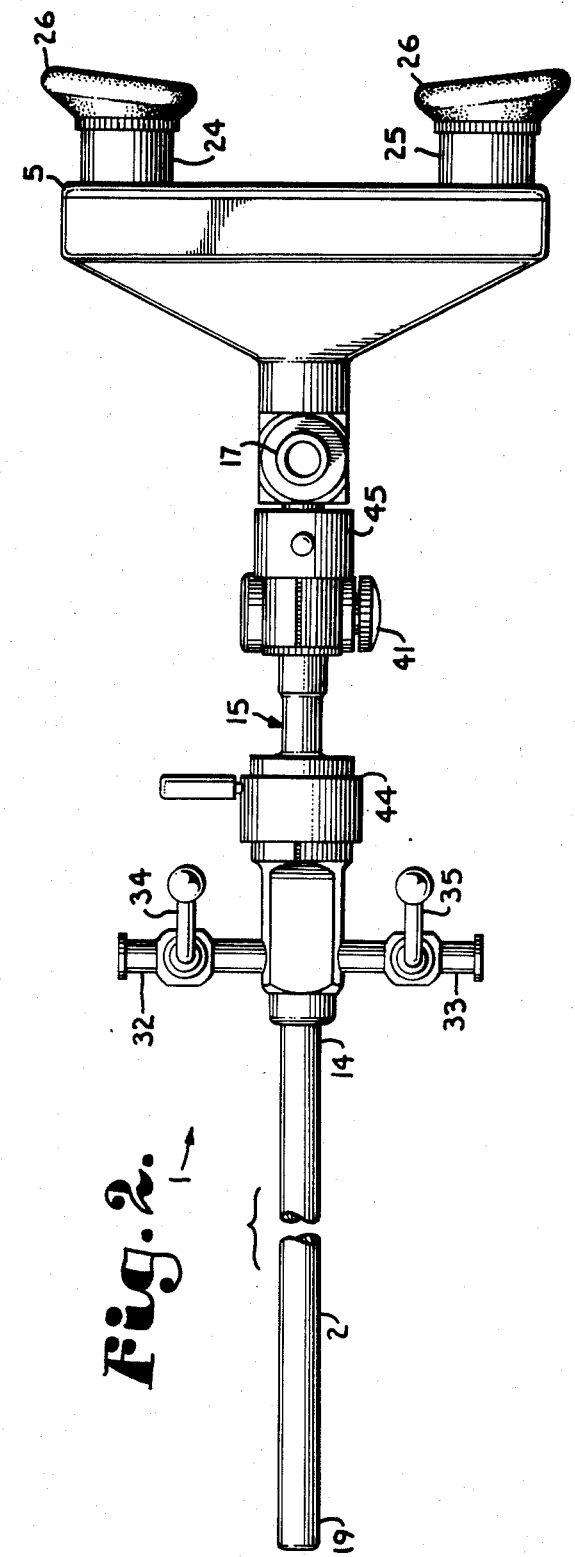

STEREOSCOPIC ENDOSCOPE ARRANGEMENT

CROSS-REFERENCE TO RELATED APPLICATIONS

The present invention is a continuation-in-part of U.S. patent application Ser. No. 616,385 for STEREOSCOPIC REMOTE VIEWING SYSTEM filed Jun. 1, 1984, and now U.S. Pat. No. 4,559,555 which was a continuation-in-part of U. S. patent application Ser. No. 351,917 for PORTABLE REMOTE TERMINAL WITH HEAD HELD DISPLAY, filed Feb. 24, 1982, now abandoned.

FIELD OF THE INVENTION

The present invention relates to endoscopic instruments and, more particularly, to a stereoscopic endoscopic instrument and a video stereoscopic endoscope with a head worn stereoscopic video display.

BACKGROUND OF THE INVENTION

Endoscopic instruments have been developed to allow physicians and surgeons to view conditions within the body and perform certain surgical procedures without the trauma, disfiguration, expense, and hazards usually associated with conventional types of surgery performed through relatively large incisions in the skin.

Endoscopes range in complexity from simple viewing scopes (employing a light source and a system of conventional lenses to transmit the image) to relatively complex endoscopes (having a light source, an image guide, several fluid channels, and a surgical tool channel). The number of features employed in an endoscope is determined in part by the requirements of the surgical specialty in which the endoscope is used and in part by the size of endoscope which can be accommodated by the body part through which the endoscope will be introduced. The light source for illuminating the site of interest is usually positioned outside the patient's body to avoid overheating the tissues. The light is communicated through the endoscope by an illumination or light guide usually formed of a fiber optic bundle. It is conceivable that the light guide could be separate from the endoscope itself. This would reduce the diameter of the endoscope or would allow additional functions in a scope of a given diameter. However, difficulties might be encountered in coordinating the positions of the light guide and the endoscope in some situations.

Endoscopes may be constructed as rigid or flexible as conditions require. The use of conventional lenses to form the image guide generally requires that the scope be rigid or semi-rigid. Flexible endoscopes employ coherent optical fiber bundles wherein the opposite ends of the fibers are identically ordered. The image quality of lens based image guides is generally superior to image guides formed of optical fibers. However, the convenience of a flexible endoscope compensates for the slight loss in resolution.

The fluid channels in endoscopes serve varied purposes. In some endoscopes for use in lungs, for example, an air passage is required to allow the lung to breathe. In certain procedures, a gas or a liquid is used to insufflate or inflate a cavity in the body for better access and a better view. In many cases, a supply of cleansing fluid such as water is used to clear away a body fluid such as blood from a location to facilitate inspection or to clean the image guide objective lens that has become smeared. A vacuum line is often provided for removing fluids from the site. The surgical tool channel provides for the insertion of various implements through the endoscope such as forceps, scissors, punches, coagulating electrodes, and the like.

A typical endoscope may include a tubular sheath connected to a frame or mechanical coupling to which viewer optics are connected. Fluid channels extending through the sheath communicate with external fluid connections on the frame and usually include valves therebetween. A tool port on the frame communicates with a tool channel in the sheath and might include a clamp to hold the tool in place. A light port connects with and receives light from a light source. The light is transmitted from the viewing end or proximal end of the endoscope to a light directing lens or lenses at the distal end. The objective lens and possibly other optical elements are positioned at the distal end and pass the image to the image guide. The objective lens is usually fixed and may be oriented along the longitudinal axis of the sheath or be angled off-axis for a view to the side. The image passes from the image guide to the viewer section of the endoscope through which the physician views the site of interest. Some endoscopes have a fixed combination of functions. Others are adapted to allow a selection of functions from a variety of surgical tools and viewing angles. In any case, endoscopes are constructed so as to allow thorough sterilization.

The viewer sections of endoscopes usually accommodate adapters for connecting motion and still cameras and video cameras. In some cases, an image splitter is employed to direct part of the image to an optical viewer for direct viewing and another part to a video camera to televise a procedure for training purposes or to record the operation or exploration for comparison with explorations from other times in the course of a treatment. However, the use of an image splitter offers a somewhat degraded pair of images for a given level of light since the light levels are divided by the image splitter.

SUMMARY OF THE INVENTION

Heretofore, known endoscopes have employed a single image guide providing only a monoscopic view of a site within a patient. The present invention provides enhanced viewing capability in an endoscope by employing a pair of image guides in a stereoscopic arrangement to transmit a three dimensional view of the site. A pair of video cameras sense the right and left images which are displayed on a head worn video stereoscopic viewer unit. Provisions are made for recording the images in analog or digital form and for redisplaying the images on the viewer unit for comparisons. The pairs of images may be distributed to other stereoscopic viewer units or monoscopically to conventional video monitors. A switch is provided for selectively displaying the images from one of the right or left image guides on both of the monitors of the viewer unit should one of the objective lenses become obscured by a structural characteristic of an organ or by a body fluid.

OBJECTS OF THE INVENTION

The principal objects of the present invention are: to provide an improved endoscopic instrument; to provide, particularly, a stereoscopic endoscope for three dimensional viewing within a portion of a patient's body for diagnostic or surgical purposes; to provide such an endoscope including right and left image guides extending through an endoscope sheath along with a light guide, one or more fluid channels, and an endoscopic surgical tool; to provide such an endoscope wherein the image guides are coupled to an optical stereoscopic viewer for direct viewing of images transmitted by the arrangement; to provide an endoscope arrangement including a pair of video cameras connected to right and left video displays or monitors of a head worn video stereoscopic viewer unit; to provide such an arrangement including a video signal switching unit for selectively displaying images from the cameras on remote video monitors; to provide such an arrangement including a monoscope/stereoscope mode switch for selectively communicating video signals from only one of the cameras to both of the video displays of the display unit for selecting an optimal monoscopic view of a site or in the event that one of the objective lenses becomes occluded; to provide such an arrangement wherein a video recorder or recorders can be connected to the video switching unit for recording the viewed images or for playing back previously recorded images on the display unit; to provide such an arrangement wherein a digital computer may be connected to the video switching unit for the digitizing and storing of the images viewed or for redisplaying such previously stored images, graphics, or text on the viewer unit; to provide such an arrangement which is adaptable to many medical fields; and to provide such a stereoscopic endoscope arrangement which is economical to manufacture, precise and durable in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of a stereoscopic endoscope instrument according to the present invention.

FIG. 2 is a top plan view of the endoscope.

DETAILED DESCRIPTION OF THE PREFERRED EMBODIMENTS

Figure 4:
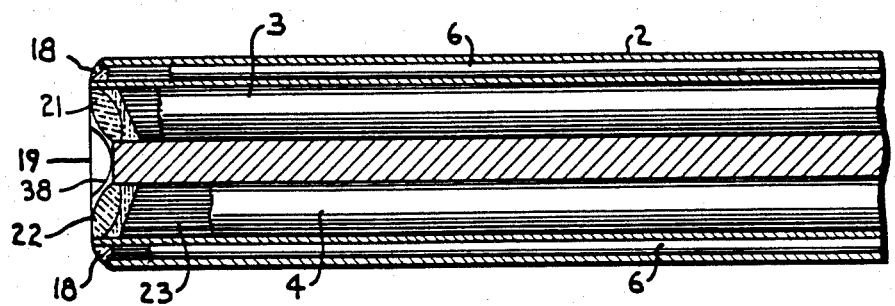
FIG. 4 is a fragmentary longitudinal sectional view taken on line 4—4 of FIG. 3 at a somewhat reduced scale and illustrates details of the image guides of the endoscope.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a stereoscopic endoscope instrument or device according to the present invention. The endoscope 1 generally includes an elongated sheath 2 for insertion into a portion of a human or animal body to view therein or to perform surgical procedures, respective right and left image guides 3 and 4 (FIG. 3) extending through the sheath 2 for gathering and transmitting images from within the body, and an optical stereoscopic viewer section 5 coupled to the image guides 3 and 4 for stereoscopic viewing of the images transmitted thereby. The endoscope 1 preferably includes an illumination or light guide 6 connected to a light source 7 (see FIG. 7) for illuminating a site within the body for viewing of conditions therein. The viewer section 5 is adapted for the attachment of respective right and left video cameras 8 and 9 (FIGS. 6 and 7) to convert the images to video signals for display on right and left video displays 10 and 11 (FIGS. 7-10) positioned in a head worn video stereoscopic viewer unit 12.

The sheath 2 is an elongated structure having a plurality of lumens (lumina) or tubular passages formed therethrough. The sheath 2 may be formed from various types of rubber or plastic and may be rigid or flexible depending on the optical system employed in the image guides 3 and 4. A proximal or near end 14 of the sheath 2 is received in an endoscope frame 15 to which is also connected the viewer section 5 of the endoscope 1. The frame 15 includes various fluid and optical couplings and mechanical fittings. Referring to FIGS. 1-5, an illumination or light port 17 is provided on the frame 15 and optically connects with the light channel 6 in the sheath 2 to pass light from the light source 7 to light directing lenses 18 at a distal or far end 19 of the sheath 2. In the illustrated endoscope 1 the fiber optic bundles of the light channels 6 are not cylindrical in cross-section, but are flattened to form sectors of a cylindrical shell to conserve space. The lenses 18 direct the light to the site viewed through the image guides 3 and 4.

The endoscope 1 may employ any type of optical system to transmit images from the distal end 19 of the scope to the viewer section 5. The illustrated endoscope 1 employs coherent fiber optic technology in the image guides 3 and 4. The image guides 3 and 4 each include at least one objective lens 21 or 22 respectively which gather respective images and pass same to a respective coherent fiber optic bundle 23. The image guides 3 and 4 extend through the sheath 2, the frame 15, and into the viewer section 5 where they diverge to couple with optical elements (not shown) in respective right and left eyepieces 24 and 25 which may include eyecups 26 to block out external light during viewing through the endoscope 1.

The image guide fiber optic bundles 23 are illustrated as being cylindrical in cross-section; however, the cross-sections could be distorted to other shapes to make the best use of the available space as long as the ends of the individual fibers are maintained in their proper relationship. Since fiber optic bundles are used for the image guides 3 and 4, the sheath 2 may be constructed of a flexible material such that the endoscope 1 is flexible overall. Alternatively, the image guides 3 and 4 can be constructed from conventional lenses for a relatively rigid arrangement especially arthroscopes.

The objective lenses 21 and 22 are illustrated in FIG. 4 as being angled to the center for viewing in the direction of a longitudinal axis of the sheath 2. Endoscope optics are usually of the fix focused type, although it is foreseen that the angle of focus for the image guides 3 and 4 could be adjustale for certain uses, especially where the focal point for viewed objects changes dramatically for a particular endoscope 1. For optimum stereoscopic viewing, the objective lenses 21 and 22 are spaced apart approximately ten percent of the distance between the lenses and the common focal point thereof. In the illustrated endoscope 1, the distal end 19 of the sheath 2 is cut off perpendicular to the longitudinal axis thereof. However, endoscopes are frequently shaped otherwise. This is true particularly when the objective lenses are oriented to view toward the side. In a similar manner, the objective lenses 21 and 22 could be oriented for an off-axis view, and the sheath 2 could be adapted accordingly. It is noted that the focusing ends of the fiber optic bundles 23 may be physically turned to a fixed position or cut at a fixed angle, as is shown, with the objective lenses 21 and 22 properly angled to give the focal length desired.

Figure 3:
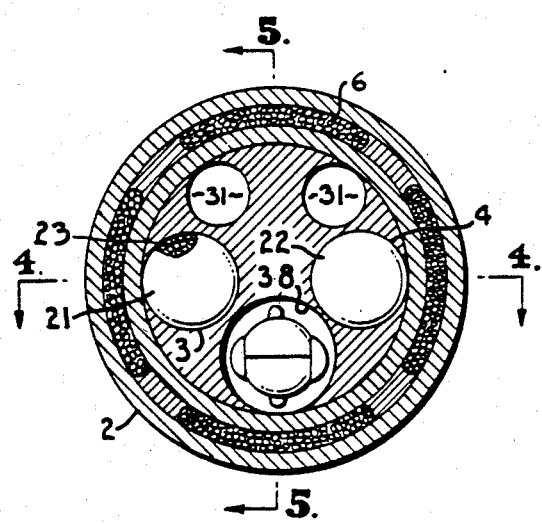
FIG. 3 is a greatly enlarged transverse sectional view through the distal end of the stereoscopic endoscope.

Referring to FIGS. 1-3, the sheath 2 may include one or more fluid channels extending therethrough, such as the fluid channels 31 illustrated in FIG. 3. The fluid channels 31 communicate respectively with fluid fittings or connectors 32 and 33 having respective valves 34 and 35 (FIG. 2.) The channels 31 may be employed for such purposes as introducing a gas into the body cavity to insufflate same or may be used to spray a cleansing fluid on the viewed site and to suction the fluid therefrom. Another purpose of the channels 31 might be to spray a cleansing fluid onto the objective lenses 21 and 22 to clear same. In such a case, the fluid channels 31 may include respective extensions and orifices (not shown) aimed toward the respective objective lenses 21 and 22.

Figure 5:
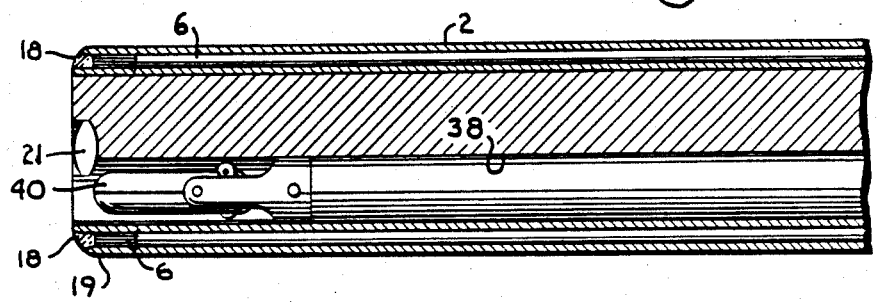
FIG. 5 is a fragmentary longitudinal sectional view taken on line 5—5 of FIG. 3 and illustrates an exemplary endoscopic surgical tool within the endoscope.

Referring to FIGS. 1, 3 and 5, a surgical tool channel 38 extends through the sheath 2 and communicates with a surgical tool port 39 extending from the endoscope frame 15. A variety of endoscopic surgical tools such as forceps, scissors, punches, and the like may be inserted into the site within the patient through the port 39 and channel 38. An exemplary forceps tool 40 is illustrated in FIG. 5 within the tool channel 38. The tool port 39 is preferably provided with a means to clamp the tool 40 in place. In the endoscope 1 illustrated in FIGS. 1 and 2, a clamp screw 41 is provided for fixing the position of the tool 40. The endoscope 1 may be inserted into the patient's body with the tool 40 in a retracted position as is shown in FIG. 5 and held therein by the clamp screw 41. When the desired surgery site has been reached, the clamp 41 may be released whereby the tool 40 may be extended to perform the desired procedure.

The endoscope frame 15 may be provided in interchangeable sections connected as by the connection collars 44 and 45 illustrated in FIGS. 1 and 2. The collars 44 and 45 may be either threaded or bayonet arrangements for interconnecting selected components for the desired procedure. For example, a sheath having additional fluid channels therein may be combined with a valve section having additional valves and fluid fittings thereon. Or a sheath having an additional surgical tool channel therein may be combined with a tool section having an additional tool port thereon. In addition, it might be desirable to include a section having a handle (not shown) thereon for better handling of the endoscope 1. In other cases, it might be desirable to include a section which allows the connection of the endoscope 1 to an adjustable arm (not shown) which holds the endoscope 1 in the desired position during the surgical procedure.

The interchangeable feature of the illustrated endoscope 1 additionally facilitates sterilization of the individual parts of the instrument. The diameter of the sheath 2 depends upon the combination of functions which are required in a particular field of surgery and also, the part of the patient's body through which the endoscope is introduced. The diameter of the sheath 2 may range from as small as four millimeters for hysteroscopy and cystoscopy to as large as 13 or 15 millimeters for upper gastrointestinal endoscopes and colonoscopes. In some surgical fields such as arthroscopy (surgery of the joints) and laparoscopy (surgery through the abdominal wall) no natural opening exists in the body for the insertion of an endoscope. For these situations, small incisions are made in the skin to provide access by an endoscope. Such incisions are usually a great deal smaller than comparable incisions required for conventional types of surgery.

Figure 6:
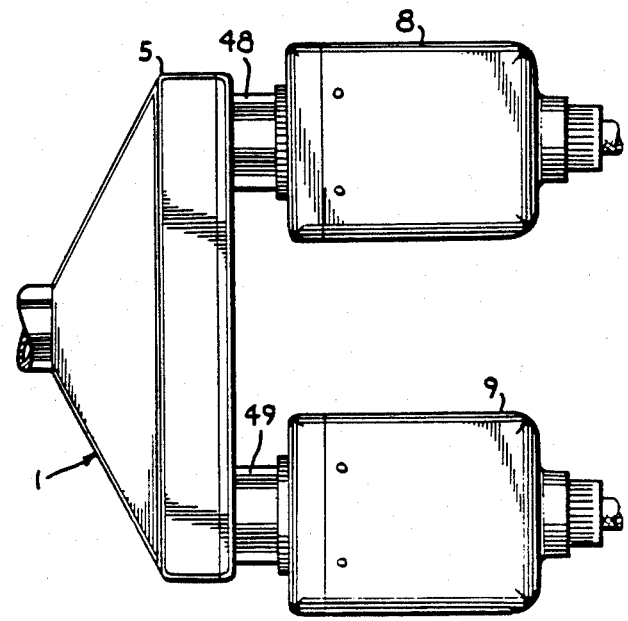
FIG. 6 is a fragmentary plan view similar to FIG. 2 and illustrates a pair of video cameras attached to a viewer section of the endoscope.

In FIG. 6, the right and left video cameras 8 and 9 are shown attached to the viewer section 5 of the endoscope 1. The eyepieces 24 and 25 are replaced respectively by camera couplers or adapters 48 and 49 which mechanically attach the cameras 8 and 9 to the viewer section 5 and couple the optical elements of the viewer section 5 to the optical elements of the cameras 8 and 9. The cameras 8 and 9 convert the received images to video signals of a standard format. The cameras may be connected more or less directly to the stereoscopic viewer unit 12, or other circuitry may intervene to provide for less direct viewing of the video images gathered by the endoscope 1.

Figure 8:
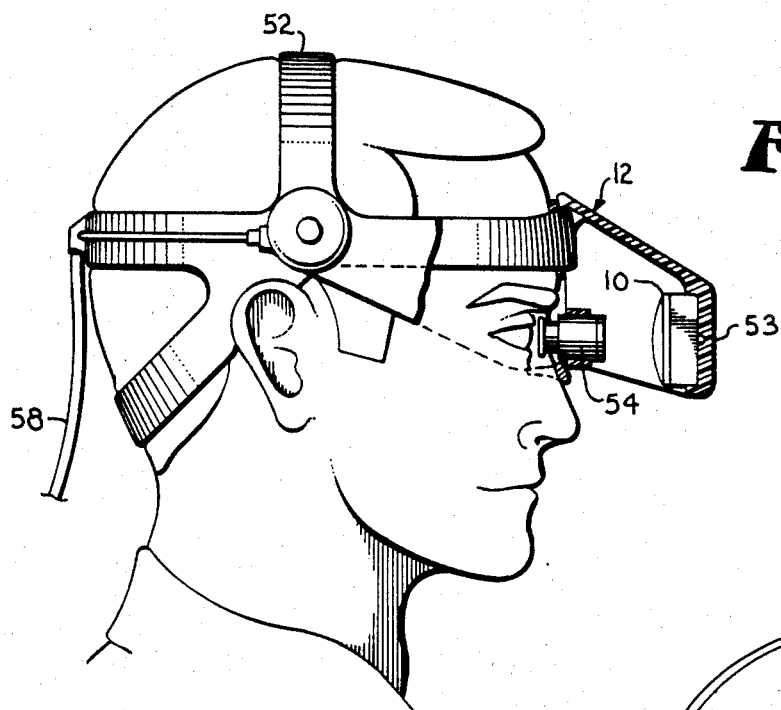
FIG. 8 is a side elevational view of a video stereoscopic viewer unit by which video images from the endoscope are stereoscopically displayed, with a portion broken away to illustrate details of the viewer unit.
Figure 9:
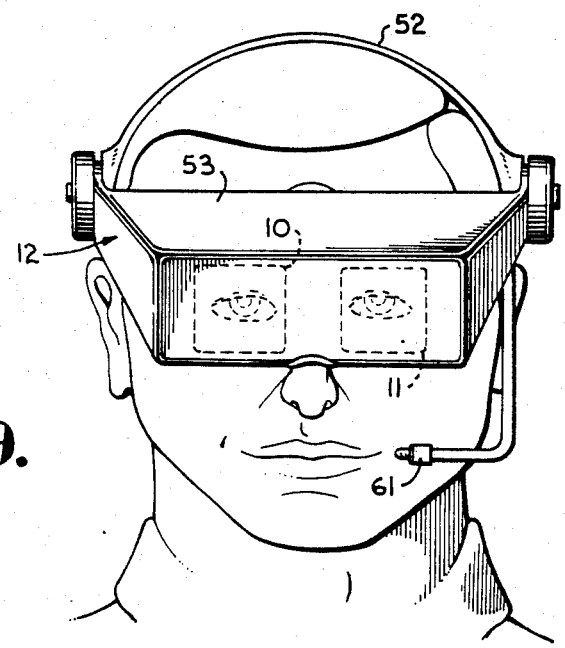
FIG. 9 is a front elevational view of the viewer unit.
Figure 10:
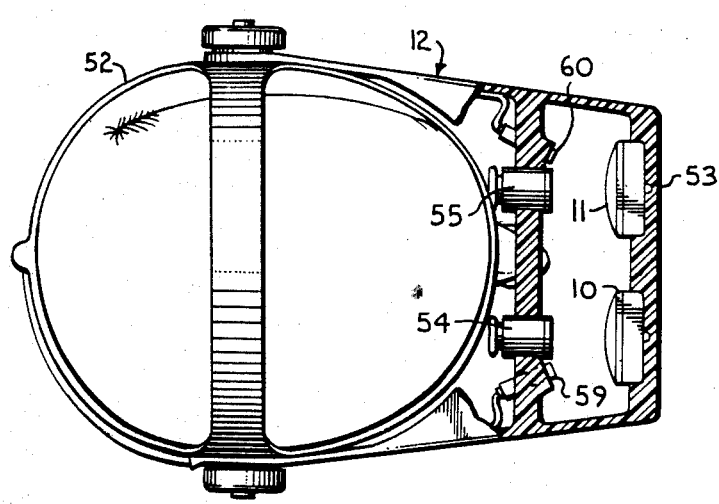
FIG. 10 is a top plan view of the viewer unit with a portion broken away to illustrate internal details.

FIGS. 8-10 illustrate an exemplary video stereoscopic viewer unit 12. The viewer unit 12 generally includes a viewer unit support harness or headband 52 to which is pivotally connected a visor 53 having the video displays 10 and 11 positioned therein. The harness 52 is preferably adjustable and is adapted for wearing on the head of a medical practitioner who is viewing the images gathered by the endoscope 1. In addition to the video displays 10 and 11, the visor 53 provides a mounting for right and left viewer unit optical elements 54 and 55 which compensate for the close spacing between the video displays 10 and 11 and the practitioner's eyes.

The illustrated video display devices 10 and 11 are liquid crystal displays (LCD), although other types of display devices such as cathode ray tubes may be utilized for this purpose. While high resolution LCD units, particularly high resolution color LCD units, are currently very expensive, and display images whose quality is often inferior to cathode ray tube (CRT) units of the same size, the reduction in weight and size of the viewer unit 12 employing LCD devices justifies their expense. The prices of high resolution and contrast LCD's are expected to trend downward due to ongoing developments in LCD technologies and also because of the employment of such displays in computers and in consumer products such as pocket television receivers. Since there is virtually no exposure of the practitioner's eyes to X-radiation with LCD's, the display devices 10 and 11 can be mounted directly in the line of sight of the practitioner. In contrast, it is generally desirable that CRT displays be viewed indirectly when viewed so close to avoid such radiation exposure. A video stereoscopic viewer unit which is suitable for use with the endoscope 1 and which employs CRT displays is described and illustrated in my copending application Ser. No. 616,385 entitled STEREOSCOPIC REMOTE VIEWING SYSTEM which is incorporated herein by reference.

It is desirable to mount a major portion of the video circuitry which drives the displays 10 and 11 elsewhere than directly on the viewer unit 12 to keep the viewer unit 12 as light as possible to avoid unnecessarily fatiguing the wearer of the unit. The video circuitry 57 (FIG. 7) is preferably mounted on a belt which is worn by the practitioner such that the video signals are conducted to the display devices 10 and 11 by means of viewer unit cables 58. The type of video circuitry required for such LCD displays would occur to one skilled in the video arts and is, therefore, not detailed here. Since LCD devices do not radiate their own light, they must be illuminated by a separate source. The LCD display devices 10 and 11 may be backlighted or, as illustrated, be illuminated reflectively by respective light sources 59 and 60 depending upon the type of LCD devices employed. The viewer unit 12 may also mount a microphone 61 by means of which a surgeon may provide a verbal commentary to the procedure in progress.

Figure 7:
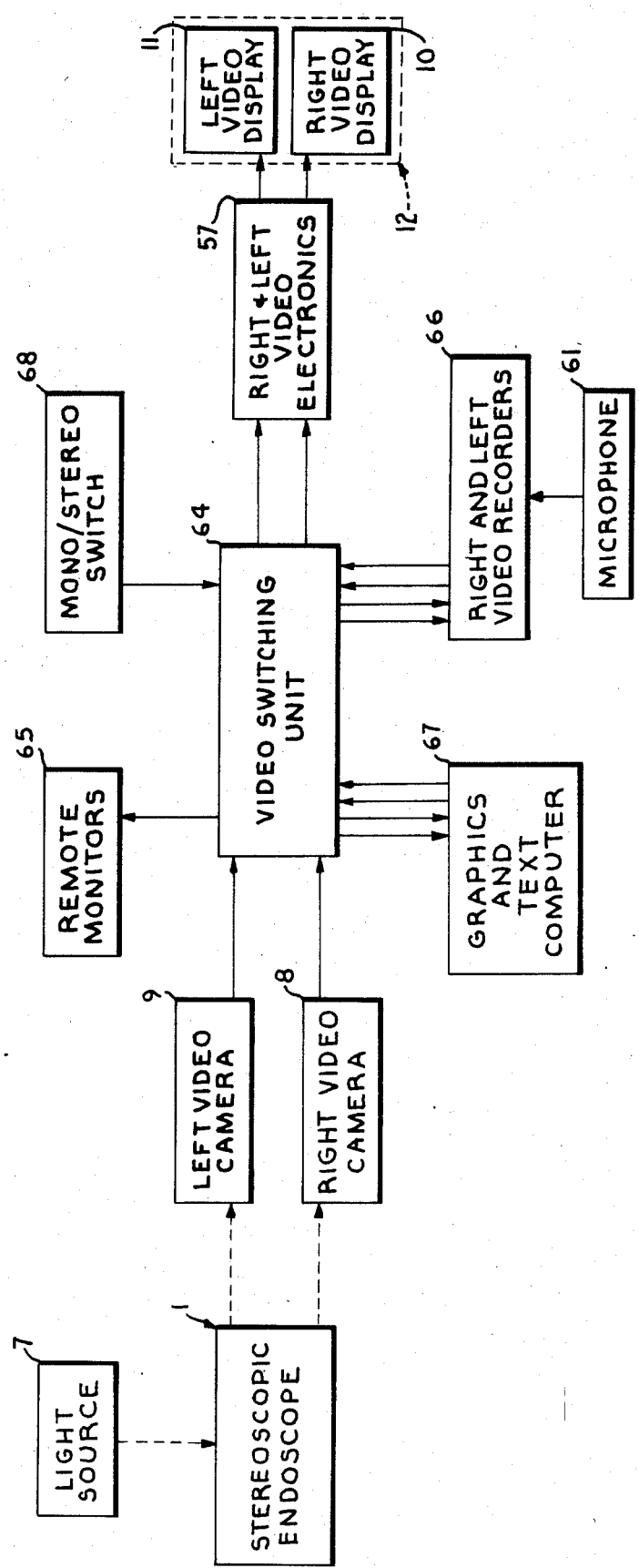
FIG. 7 is a block diagram showing the major electronic components of the stereoscopic endoscope arrangement according to the present invention.

Referring to FIG. 7, the light source 7 is preferably adjustable to allow an optimum illumination level within the patient without excessive heat. The illustrated video cameras 8 and 9 are preferably connected through a video signal switching unit 64 to the right and left video circuitry 57. The unit 64 is fairly conventional in itself and includes video distribution amplifiers for selectively distributing the video signals to remote video monitors 65, right and left video recorders 66 and a graphics and text computer 67. The remote monitors 65 may be employed for training surgeons in endoscopic diagnosis and surgical techniques. The video recorders 66 allow the recording of endoscopic explorations and surgery for subsequent consultations with other physicians, comparison of conditions at various times during a course of treatment, or for training purposes. For stereoscopic viewing of the recorded images, it is necessary that the left and right images be synchronized. This may be accomplished by using specially designed multiple track video recording machines, or by the synchronization of separate recording units for the left and right signals. The recorders could be synchronized by means of address tracks recorded on separate tapes which control the drive motors of the recording units. The microphone 61 may be connected more or less directly to the remote monitors 65 or may be connected to the video recorders for recording the surgeon's commentary.

The computer 67 may be employed for digitizing and storing images received from the endoscope 1 through the cameras 8 and 9. Digital storing of the endoscope images may be done in some circumstances for computer enhancement of the images. Such techniques may be employed for computerized diagnosis in conjunction with more conventional approaches. The provision of the computer 67 also provides for the use of very high capacity storage techniques such as laser discs when such technologies have been developed to the point that recordings can be economically made other than in a manufacturing situation.

The connections of the video recorders 66 and computer 67 are bilateral such that these devices may serve as video sources of images to be displayed on the viewer unit 12. For example, simplified diagrams and text may be displayed from the computer 67 as, for example, in the training of surgeons in new surgical techniques. In some cases, the images from the recorders 66 and 67 would not benefit from a stereoscopic display thereof. For this purpose, a mono/stereo switching arrangement 68 is provided to apply either the right or left signals to both of the video displays 10 and 11. This capability is also useful in regard to the images provided by the endoscope 1. In some situations, one of the objective lenses 21 or 22 may become obscured by structural characteristics of an organ in which the endoscope 1 has been placed or from other causes. In such a case, a view of the site of interest could still be maintained, although monoscopically, by applying the image from the unobscured objective lens to both of the video displays 10 and 11.

It is to be understood that while certain forms of the present invention have been illustrated and described herein, it is not to be limited to the specific forms or arrangement of parts described and shown.

What is claimed and desired to be secured by Letters Patent is:

1. An apparatus for viewing an interior body cavity; said apparatus comprising:
    (a) an endoscope having a first end adapted to be inserted into the body cavity and a second end external of the cavity when said first end is therein;
    (b) optic means passing through said endoscope; said optic means gathering an image at said first end and communicating said image to said second end;
    (c) video camera means operably receiving said image from said optic means and converting said image to a signal;
    (d) viewing means operably coupled with said camera means for receiving said signal and having a miniature video monitor for displaying an image represented by said signal; and
    (e) a head worn harness having said monotor mounted thereon to operatively transfer images displayed thereon to the eyes of a viewer wearing said harness, said harness being adapted such that said viewing means is supported entirely by the head of said viewer.

2. A stereoscopic endoscope device comprising:
    (a) an elongated sheath having a distal end for insertion into a body cavity and a proximal end for viewing within said body cavity therethrough;
    (b) right and left optic means oriented in spaced apart relation at said distal end and extending through said sheath and positioned to gather right and left images at said distal end and further communicating said images to proximal end;

(c) stereoscopic viewing means optically coupled to said right and left optic means for stereoscopic viewing of said images;

(d) a right video camera and a left video camera optically coupled respectively to said right and left optic means and converting images sensed therethrough to respective electronic video signals;

(e) said stereoscopic viewing means including a miniature right video monitor and a miniature left video monitor connected respectively to said right and left cameras for displaying images represented respectively by said video signals, said monitors being positioned for stereoscopic viewing of the images gathered by said optic means;

(f) video signal switching means interconnected between said cameras and said monitors, said switching means providing access to said video signals and providing for the display on said monitors of images represented by video signals other than said video signals representing images gathered by said optic means; and (g) mono/stereo switch means connected to said video signal switching means and selectively operable to communicate the video signals from one of said cameras to both of said right and left monitors.

3. A stereoscopic endoscope device comprising:

(a) an elongated sheath having a distal end for insertion into a body cavity and a proximal end for positioning external of said cavity allowing viewing within said body cavity therethrough;

(b) light channel means extending through said sheath and communicating light to said distal end for illumination of said body cavity;

(c) a light source optically connected to said light channel means and supplying light therethrough for illumination within said body cavity;

(d) right and left optic means positioned in spaced apart relation at said distal end and extending thorugh said sheath for gathering right and left images at said distal end and communicating said images to said proximal end;

(e) a right video camera and a left video camera optically coupled respectively to said right and left optic means and converting images sensed therethrough to respective electronic video signals; and (f) stereoscopic viewing means optically coupled to said right and left optic means for stereoscopic viewing of said images and including a miniature right video monitor and a miniature left video monitor connected respectively to said right and left cameras for displaying images represented respectively by said video signals, said monitors being positioned for stereoscopic viewing of the images gathered by said optic means;

(g) video signal switching means interconnected between said cameras and said monitors, said switching means providing access to said video signals and providing for the display on said monitors of images represented by video signals other than said video signals representing images gathered by said optic means; and (h) mono/stereo switch means connected to said video signal switching means and selectively operable to communicate the video signals from one of said cameras to both of said right and left monitors.

4. A stereoscopic endoscope device comprising:

(a) an elongated sheath having a distal end for insertion into a body cavity and a proximal end for positioning external of said cavity to allow viewing within said body cavity;

(b) right and left optic means positioned in spaced apart relation at said distal end to gather right and left images at said distal end, extending through said sheath, and communicating said images to said proximal end;

(c) a right video camera and a left video camera optically coupled respectively to said right and left optic means and converting images sensed therethrough to respective electronic video signals;

(d) stereoscopic viewing means including a miniature right video monitor and a miniature left video monitor connected respectively to said right and left cameras to display images represented respectively by said video signals, said monitors being positioned for stereoscopic viewing of the images gathered by said optic means; and (e) video signal switching means interconnected between said cameras and said monitors, said switching means providing access to said video signals and providing for the display on said monitors of images represented by video signals other than said video signals representing images gathered by said optic means.

5. A device as set forth in claim 4 including:

(a) a remote video monitor selectively interconnected with one of said video cameras through said video signal switching means for displaying images sensed by one of said cameras at a location remote from said cameras.

6. A device as set forth in claim 14 including:

(a) computer means interconnected with said video signal switching means for digitizing and storing said images and for retreiving previously digitized and stored images and texts from said computer means for display on said monitors.

7. A device as set forth in claim 4 including:

(a) video recorder means connected to said video signal switching means for recording signals representing said images and for playing back previously recorded video images for display on said monitors.

8. A stereoscopic endoscope device comprising:

(a) an elongated sheath having a distal end for insertion into a body cavity and a proximal end for positioning external of said cavity to allow viewing within said body cavity therethrough;

(b) light channel means extending through said sheath and communicating light to said distal end for illumination of said body cavity;

(c) a light source optically connected to said light channel means and supplying light therethrough for illumination within said bocy cavity;

(d) right and left optic means positioned in spaced apart relation at said distal end and extending through said sheath for gathering right and left images at said distal end and communicating said images to said proximal end;

(e) a right video camera and a left video camera optically coupled respectively to said right and left optic means and converting images sensed therethrough to respective electronic video signals;

(f) stereoscopic viewing means optically coupled to said right and left optic means for stereoscopic viewing of said images and including a miniature right video monitor and a miniature left video monitor connected respectively to said right and left cameras for displaying images represented respectively by said video signals, said monitors being positioned for stereoscopic viewing of the images gathered by said optic means; and (g) video signal switching means interconnected between said cameras and said monitors, said switching means providing access to said video signals and providing for the display on said monitors of images represented by video signals other than said video signals representing images gathered by said optic means.

9. A device as set forth in claim 8 including:
(a) a remote video monitor selectively interconnected with one of said video cameras through said video signal switching means for displaying images sensed by one of said cameras at a location remote from said cameras.

10. A device as set forth in claim 8 including:
(a) computer means interconnected with said video signal switching means for digitizing and storing said images and for retreiving previously digitized and stored images and texts from said computer means for display on said monitors.

11. A device as set forth in claim 8 including:
(a) video recorder means connected to said video signal switching means for recording signals representing said images and for playing back previously recorded video images for display on said monitors.

12. A stereoscopic endoscope device comprising:
(a) an elongated sheath having a distal end for insertion into a body cavity and a proximal end for positioning external of said cavity to allow viewing within said body cavity therethrough;
(b) light channel means extending through said sheath and communicating light to said distal end for illumination of said body cavity;
(c) a light source optically connected to said light channel means and supplying light therethrough for illumination within said body cavity;
(d) right and left optic means positioned in spaced apart relation at said distal end and extending through said sheath for gathering right and left images at said distal end and communicating said images to said proximal end;
(e) a right video camera and a left video camera optically coupled respectively to said right and left optic means and converting images sensed therethrough to respective electronic video signals;
(f) stereoscopic viewing means including a miniature right video monitor and a miniature left video monitor connected respectively to said right and left cameras for displaying images represented respectively by said video signals, said monitors being positioned for stereoscopic viewing of the images gathered by said optic means; and
(g) a head worn harness having said video monitors mounted thereon to operatively transfer the images displayed respectively thereon to the right and left eyes of a viewer wearing said harness, said harness being adapted such that said viewing means is supported entirely by the head of the viewer.

13. A device as set forth in claim 12 wherein:
(a) said optic means includes a pair of flexible, coherent fiber optic image guides; and
(b) said sheath is flexible whereby said endoscope arrangement is flexible.

14. A device as set forth in claim 12 wherein:
(a) said video cameras are color video cameras; and
(b) said video monitors are color video monitors.

15. A device as set forth in claim 12 including:
(a) a surgical tool channel extending through said sheath for insertion of an endoscopic surgical tool therethrough into said body cavity.

16. A device as set forth in claim 12 including:
(a) at least one fluid channel extending through said sheath for the communication of a fluid with said body cavity.

17. A device as set forth in claim 16 including:
(a) a fluid valve positioned in said fluid channel for controlling the flow of said fluid through said fluid channel.

18. A stereoscopic endoscope device comprising:
(a) an elongated sheath having a distal end for insertion into a body cavity and a proximal end for positioning external of said cavity to allow viewing within said body cavity;
(b) right and left optic means positioned in spaced apart relation at said distal end to gather right and left image at said distal end, extending through said sheath, and communicating said images to said proximal end;
(c) a right video camera and a left video camera optically coupled respectively to said right and left optic means and converting images sensed therethrough to respective electronic video signal;
(d) stereoscopic viewing means including a miniature right video monitor and a miniature left video monitor connected respectively to said right and left cameras to display images represented respectively by said video signals, said monitors being positioned for stereoscopic viewing of the images gathered by said optic means; and
(e) light source means including light channel means extending through said sheath to illuminate said body cavity for viewing therein.

19. A device as set forth in claim 18 wherein said stereoscopic viewing means includes:
(a) a head worn harness having said video monitors mounted thereon to operatively transfer the images displayed respectively thereon to the right and left eyes of a viewer wearing said harness.

20. A device as set forth in claim 18 wherein:
(a) said optic means includes a pair of flexible, coherent fiber optic image guides; and
(b) said sheath is flexible whereby said endoscope device is flexible.

21. A device as set forth in claim 18 wherein:
(a) said video cameras are color video cameras; and
(b) said video monitors are color video monitors.

22. A device as set forth in claim 18 including:
(a) a surgical tool channel extending through said sheath for insertion of an endoscopic surgical tool therethrough into said body cavity.

23. A device as set forth in claim 18 including:
(a) at least one fluid channel extending through said sheath for the communication of a fluid with said body cavity.

24. A device as set forth in claim 23 including:
(a) a fluid valve positioned in said fluid channel for controlling the flow of said fluid through said fluid channel.

* * * * *